United States Patent [19]
Prudhoe

[11] Patent Number: 5,814,339
[45] Date of Patent: Sep. 29, 1998

[54] FILM COATED TABLET OF PARACETAMOL AND DOMPERIDONE

[75] Inventor: Gordon Prudhoe, Newcastle-Upon-Tyne, England

[73] Assignee: Janssen Pharmaceutica, N.V., Beerse, Belgium

[21] Appl. No.: 652,514

[22] PCT Filed: Feb. 27, 1995

[86] PCT No.: PCT/EP95/00719

§ 371 Date: Jun. 4, 1996

§ 102(e) Date: Jun. 4, 1996

[87] PCT Pub. No.: WO95/22974

PCT Pub. Date: Aug. 31, 1995

[30] Foreign Application Priority Data

Feb. 28, 1994 [EP] European Pat. Off. ............. 94200498

[51] Int. Cl.$^6$ ................................ A61K 9/32; A61K 9/36
[52] U.S. Cl. ........................... 424/480; 424/474; 424/482
[58] Field of Search ................................ 424/464, 489, 424/480, 470, 474, 482

[56] References Cited

U.S. PATENT DOCUMENTS 5,273,759  12/1993  Simmons ................................. 424/465
5,456,920  10/1995  Matoba et al. ........................... 424/465
5,587,179  12/1996  Gergley et al. .......................... 424/466
5,618,828   4/1997  Gray et al. ............................... 514/327

FOREIGN PATENT DOCUMENTS 0 011 490 A2   5/1980  European Pat. Off. ......... A61K 9/20
0 011 490 B2  10/1989  European Pat. Off. ......... A61K 9/20

OTHER PUBLICATIONS

*Cephalagia*, 13 (2), pp. 124–127, MacGregor et al., "Domperidone plus paracetamol in the treatment of migraine".

*S. Afr. J. Sci.*, 1988, p. 431, Van der Merve et al., "Domperidone reduces the accumulation of paracetamol in saliva".

The Martindale 30th Edition, p. 883.2, "Domperidone".

*Primary Examiner*—Thurman K. Page
*Assistant Examiner*—William E. Benston, Jr.
*Attorney, Agent, or Firm*—Ellen Ciambrone Coletti

[57] ABSTRACT

The present invention is concerned with a film coated tablet comprising as active ingredients the analgesic agent paracetamol and the antiemetic agent domperidone, and with a process of preparing such tablets.

11 Claims, No Drawings

FILM COATED TABLET OF PARACETAMOL AND DOMPERIDONE

CROSS-REFERENCE TO RELATED APPLICATIONS

This application is based upon PCT Application Ser. No. PCT/EP 95/00719, filed Feb. 27, 1995, which claims priority from European Patent Application Ser. No. 94.200.498.7, filed on Feb. 28, 1994.

The present invention is concerned with a film coated tablet comprising as active ingredients the antipyretic analgesic paracetamol and the antiemetic agent domperidone, and with a process of preparing such tablets.

In Cephalalgia 13 (2), 124–7 (1993) the safety and efficacy of separately administered domperidone in combination with paracetamol in the treatment of migraine, especially acute attacks of migraine is disclosed. Paracetamol is an effective analgesic similar in efficacy to aspirin but less irritant to the stomach. Its normal unit dose is about 500 mg b.i.d., t.i.d. or q.i.d. Domperidone is a peripheral dopamine antagonist effective as an anti-nauseant which is thought not to cross the blood brain barrier, and because of this, not to be likely to cause extrapyramidal side effects. It promotes the gastrointestinal motility and thus could enhance the rate of paracetamol absorption which is sometimes slowed by the mild gastroparesis that may accompany migraine attacks. Its normal unit dose is about 10 mg o.d., b.i.d. or t.i.d.

Up till now, domperidone and paracetamol have been administered as separate dosage forms, but if the two were available as one preparation, as a single tablet for instance, patients would find such an administration form more convenient and would be expected to take the medicine more readily and in the earlier stages of a migraine attack. It is advantageous to start the treatment of a migraine attack at the earliest possible moment as it is then more likely to be effective.

The mere combination of domperidone granules with paracetamol granules such as are used each individually for preparing the art-known single formulations, is conceivably the most simple solution, but fails because it yields large unit dosage forms of about 700 mg which most patients find difficult or impossible to swallow. Indeed, paracetamol crystals are hard, brittle and fracture easily, and consequently can be tabletted only using relatively high amount of excipients. Moreover, for easy oral administration, large tablets should preferably be film coated which yet again increases the tablet size. The present invention therefore seeks to solve the above-mentioned problems by providing an acceptable film coated tablet having the smallest possible size and yet containing the required dose of about 500 mg paracetamol and about 10 mg domperidone per unit dosage form.

In particular the composition of the present invention concerns a tablet comprising (a) a core comprising paracetamol and domperidone as the active ingredients, and a pharmaceutically acceptable carrier, and (b) a film coat.

Such tablets represent a unit dosage form and comprise about 500 mg paracetamol and about 10 mg domperidone in the core. In the finished film coated tablets according to the present invention, the total tablet weight is about 620–625 mg ±5%, 500 mg (ca. 80%) of which is paracetamol and 10 mg (ca. 1.6%) of which is domperidone. Thus the amount of tabletting aids is below 20% (w/w) of the total tablet weight.

Tablets for humans having a lower bodyweight may be only half as large and comprise about 250 mg paracetamol and about 5 mg domperidone in the core.

The (1:1) maleate salt of domperidone is preferred as opposed to the base because in the solid dosage form of the present invention better bioavailability is obtained. 10 mg domperidone corresponds to 12.72 mg of domperidone maleate.

The pharmaceutically acceptable carrier comprises one or more solid diluents, disintegrants, tablet binding agents, granulating agents, and optionally other formulating agents known in the art such as, for example, suspending agents, dispersing agents, solvents, flow aids, glidants, anticaking agents, preservatives or lubricants. Carrier compounds may have several functions in the tablets: ingredients used mainly for one particular property may well function also as compounds typical of another class.

The solid diluent or carrier in the core of the tablet can be selected from for example sucrose, lactose (coarse, regular, anhydrous, spray-dried), trehalose, maltose, mannitol, sorbitol, starches (corn, wheat, maize, potato), starch hydrolysates, pregelatinized starch (thermally, mechanically or chemically modified), microcrystalline starches, microcrystalline cellulose. It is preferably pregelatinized starch and its amount can range from about 7% to about 10%, especially about 8% by weight of the total tablet weight.

Disintegrants facilitate the breakup of a tablet after administration. They may be added prior to granulation or during the lubrication step prior to compression, or as in the instant case at both processing steps. The intergranular (or extragranular) disintegrant (i.e. the one added during the lubrication step) causes tablet rupture. The intragranular disintegrant effects the fine distribution of the particles constituting the granulate. The most common disintegrants are starches, whether natural (corn, wheat, maize, potato) or pregelainized. Preferably maize starch is used as a disintegrant in an amount ranging from 3% to 4%, especially about 3.5% by weight of the total tablet weight.

Tablet binding agents or binders or granulating agents can be selected from cellulose derivatives, gelatin, pregelatinized starch, starch paste, glucose, sucrose, sorbitol, polyvinylpyrrolidone (polyvidone ), tragacanth, acacia, sodium alginate or combinations thereof.

Preferably polyvidone is used as a granulating agent as it compresses very well and because a wet granulation process is called for in the instant case. Its amount ranges from 0. 1% to 0.4%, especially about 0.3% by weight of the total tablet weight. Preferably water is used in conjunction as a wetting agent.

Among the optional formulating agents that further may be comprised in the core of the tablet there may be mentioned agents such as flow aids e.g. talc, preferably purified talc; glidants such as colloidal silica; lubricants such as stearic acid, magnesium stearate and/or paimitate; antiadherents such as talc and corn starch; polyvidone also having suspending and dispersing properties; solvents, in particular those used during the preparation, e.g. water and lower alcohols such as ethanol and isopropanol. Usually one lubricant is sufficient but the use of a combination of two, namely stearic acid and magnesium stearate benefits the manufacture of this particular formulation.

The film coat covering the core of the tablet should be designed in such a manner that it dissolves rapidly upon ingestion. Preferably the film coat is opacified, especially with a pigment, e.g. titanium dioxide. The film coat comprises a hydrophilic polymer such hydroxypropyl methylcellulose, e.g. hypromellose 2910 5mPa.s and a plasticizer such as polyethylene glycol in a ratio from 6:1 to 4:1, preferably about 5:1 (w/w).

The preferred tablets comprise approximately
(a) in the core
500 mg paracetamol
12.72 mg domperidone maleate (10 mg domperidone)
50 mg pregelatinized starch
22 mg maize starch
2 mg polyvidone
15 mg talc (purified)
5 mg stearic acid
1 mg magnesium stearate
(b) in the film coat:
10 mg hydroxypropyl methylcellulose
2 mg polyethylene glycol 400
3.20 mg titanium oxide The tablets, in particular the preferred ones, can conveniently be manufactured by a wet granulation route, followed by dry blending, compression and film coating. Wet granulation is used to blend the two active ingredients in order to ensure that the relatively low dose of domperidone is fairly distributed during the manufacturing process and thus that each unit dosage form contains a similar amount of domperidone. The other wet granulation ingredients are the granulation agent polyvidone, pregelatinized starch as the solid diluent and part of the maize starch (about 50–60%) as the intragranular disintegrant. These ingredients are thoroughly mixed in a high speed mixer. Purified water is added and mixing is continued until a light granular mass is formed, which is then dried in a fluid bed drier.

The present invention thus also concerns a granular mixture suitable for use in the manufacture of a tablet comprising paracetamol and domperidone as the active ingredients, characterized in that both active ingredients are in intimate physical admixture. In a further aspect, the invention concerns the use of a granular mixture comprising paracetamol and domperidone for the manufacture of a medicament, in particular a medicament for the treatment of migraine.

The dry blend ingredients are talc, magnesium stearate, stearic acid, and the remainder of the maize starch. At this stage the maize starch functions as an intergranular disintegrant. The other ingredients are present to enhance flow and provide lubrication. The dried granules are passed through a suitable screen along with the dry blend ingredients, collected in a stainless steel container and the mixture is well blended until homogeneous. The mixture is compressed to tablets having a nominal compression weight of 607.72 mg ±5%. The tablet can be shaped in various ways, e.g. as a flat disc with an essentially circular cross section, or as preferred in the instant case, as an oblong tablet which is easier to swallow. The tablet can be scored so as to facilitate its breaking into two halves.

The film coat is prepared by adding the hydrophilic polymer and the plasticizer to a stirred amount of water. 25 % of the solution is removed and retained. To the remaining solution titanium dioxide is added and mixed until homogeneous. The compressed tablets are charged into a coating pan. The pigmented seal coating solution is sprayed onto the tablets and upon completion the white film coated tablets are coated with the retained clear coating solution. The coated tablets are packed into PVC/aluminium foil blister packs. The coated tablets have a hardness ranging from 6 to 12 kilopascal (kP), preferably from about 7 to about 9 kP.

Using the process parameters described above, a convenient, reproducible manufacturing method for preparing film coated tablets of paracetamol and domperidone maleate can be obtained. Pharmacokinetic studies unexpectedly show that the systemic bioavailability of domperidone when administered in the new tablet formulation of the present invention is approximately 30% to 40% higher than when administered via the art-known domperidone tablets. The plasma concentration of paracetamol on the other hand is not significantly affected by the presence of domperidone. Effective plasma levels of both active ingredients are maintained for at least several hours.

The present invention also concerns a method for treatment of a patient suffering from migraine, which method comprises administering to the patient a therapeutically effective amount of a medicament comprising a granular mixture of paracetamol and domperidone as described hereinbefore. In particular, the method comprises administering a tablet manufactured from said granular mixture in the manner described above.

EXAMPLE 1 a) Preparation of the tablet core.

Paracetamol, domperidone maleate, pregelatinized starch, about half of the maize starch and polyvidone were sieved and blended together in a high speed mixer. Purified water (about 25 % w/w of paracetamol) was added and the whole was mixed until a light granular mass was formed which was then dried in a fluid bed drier. The dried granules were passed through a dry screen into the stainless steel container of a blender. The remainder of the maize starch, talc, stearic acid and magnesium stearate were passed through a sieve into the same container and blended with the granulate until uniform. The blend was compressed on a rotatory compression machine to tablets having a nominal weight of 607.72 mg ±5%.

b) Preparation of the seal coating solution

Hydroxypropyl methylcellulose was added to purified water and mixed until completely dispersed. The solution was left to stand until clear. Polyethylene glycol 400 was added and mixed until uniform. A quarter of the solution was removed and retained. Titanium dioxide was added to the remaining solution and mixed until uniform.

c) Coating of the tablet core

The tablet cores were placed in a coating pan and the pigmented coating solution was sprayed onto the cores. Upon completion, the white film coated cores were coated with the retained clear coating solution. Average tablet weight was 622.9 mg ±5%.

d) Packing

The coated tablets were packed into polyvinylchloride/ aluminium foil blister packs, which in turn were packed into cardboard cartons.

e) Properties

The coated tablets had a disintegration time of not greater than 10 minutes and friability was such that not more than 1% weight loss occurred. Minimum hardness was 7, preferably 8 kP.

EXAMPLE 2

The bioavailability study was a three way crossover study in twelve healthy human volunteers in which the instant tablets, paracetamol tablets and domperidone tablets were compared at a dose of two tablets equivalent to 1000 mg paracetamol and/or 25.44 mg domperidone maleate. Comparison of the paracetamol data showed the following:

|  | the instant tablets | paracetamol tablets |
|---|---|---|
| $C_{max}$ (μg/ml) | 20.1 | 17.7 |
| $T_{max}$ (h) | 0.64 | 0.42 |
| AUC (0-$t_n$) (μg/ml.h) | 49.2 | 52.8 |

The only factor that proved to be statistically significant was $T_{max}$ which was significantly longer for the instant tablets. This can be explained by the effect of the film coat somewhat delaying the release of the drug in vivo by up to 15 minutes.

Otherwise the behaviour of paracetamol in the instant tablets was as anticipated with comparable $C_{max}$ and AUC figures with paracetamol tablets. A similar comparison of the domperidone data showed the following:

|  | the instant tablets | domperidone tablets |
|---|---|---|
| $C_{max}$ (μg/ml) | 43.9 | 19.1 |
| $T_{max}$ (h) | 0.64 | 0.95 |
| AUC (0-$t_n$) (μg/ml.h) | 92.9 | 66.5 |

The faster $T_{max}$ for the instant tablets is due to the thinner film coat delaying the release of the drug to a lesser extent than from domperidone tablets.

However both the $C_{max}$ and AUC results show enhanced bioavailability of domperidone from the instant tablets compared to domperidone tablets with the AUC (0-$t_n$) being some 40% greater for the instant tablets.

I claim:

1. A tablet comprising
   (a) a core comprising paracetamol and domperidone as the active ingredients and a pharmaceutically acceptable carrier, and
   (b) a film coat; wherein the amount of pharmaceutically acceptable carrier is below 20% (w/w) of the total tablet weight.

2. A tablet according to claim 1 wherein the pharmaceutically acceptable carrier comprises one or more solid diluents, disintegrants, tablet binding agents, granulating agents.

3. A tablet according to claim 2 wherein the pharmaceutically acceptable carrier further comprises other formulating agents such as flow aids, glidants, anticaking agents, preservatives, lubricants, suspending agents, dispersing agents.

4. A tablet according to claim 1 wherein the core comprises about 500 mg paracetamol and about 10 mg domperidone.

5. A tablet according to claim 1 wherein the domperidone is in the (1:1) maleate salt form.

6. A tablet according to claim 1 wherein the core comprises the two lubricants stearic acid and magnesium stearate.

7. A tablet according to claim 1 wherein the film coat is rapidly dissolving upon ingestion and is opacified.

8. A tablet according to claim 7 wherein the film coat comprises a hydrophilic polymer, a plasticizer and a pigment.

9. A tablet according to any one of claims 1 to 8 comprising approximately
   (a) in the core
       500 mg paracetamol
       12.72 mg domperidone maleate
       50 mg pregelatinized starch
       22 mg maize starch
       2 mg polyvidone
       15 mg talc (purified)
       5 mg stearic acid
       1 mg magnesium stearate
   (b) in the film coat:
       10 mg hydroxypropyl methylcellulose
       2 mg polyethylene glycol 400
       3.20 mg titanium oxide.

10. A method for treatment of a patient suffering from migraine, which method comprises administering to the patient a therapeutically effective amount of a medicament comprising a granular mixture of paracetamol and domperidone as the active ingredients, wherein both active ingredients are in intimate physical admixture.

11. A method for treatment of a patient suffering from migraine, which method comprises administering to the patient a tablet as defined in claim 1.

* * * * *